US011359222B2

(12) United States Patent
Tao et al.

(10) Patent No.: US 11,359,222 B2
(45) Date of Patent: Jun. 14, 2022

(54) ENZYMATIC METHOD FOR PREPARING REBAUDIOSIDE J

(71) Applicant: PepsiCo, Inc., Purchase, NY (US)

(72) Inventors: Alex Tao, Jiangsu (CN); Guoqing Li, Jiangsu (CN); Wenxia Wang, Jiangsu (CN); Leilei Zheng, Jiangsu (CN); Chunlei Zhu, Jiangsu (CN); Xiaoliang Liang, Jiangsu (CN); Kuikiu Chan, Jiangsu (CN)

(73) Assignee: PepsiCo, Inc., Purchase, NY (US)

( * ) Notice: Subject to any disclaimer, the term of this patent is extended or adjusted under 35 U.S.C. 154(b) by 365 days.

(21) Appl. No.: 16/343,340

(22) PCT Filed: Oct. 21, 2016

(86) PCT No.: PCT/CN2016/102942
§ 371 (c)(1),
(2) Date: Apr. 18, 2019

(87) PCT Pub. No.: WO2018/072211
PCT Pub. Date: Apr. 26, 2018

(65) Prior Publication Data
US 2019/0338332 A1 Nov. 7, 2019

(51) Int. Cl.
*C12P 19/56* (2006.01)
*C12N 9/10* (2006.01)

(52) U.S. Cl.
CPC ............ *C12P 19/56* (2013.01); *C12N 9/1051* (2013.01); *C12Y 204/01017* (2013.01)

(58) Field of Classification Search
None
See application file for complete search history.

(56) References Cited

U.S. PATENT DOCUMENTS

| 9,243,273 | B2 | 1/2016 | Markosyan et al. |
| 9,752,174 | B2 | 9/2017 | Markosyan |
| 10,301,662 | B2 | 5/2019 | Tao et al. |
| 2010/0099857 | A1 | 4/2010 | Evans |
| 2011/0218161 | A1 | 9/2011 | Han et al. |
| 2013/0171328 | A1 | 7/2013 | Kishore et al. |
| 2014/0271996 | A1 | 9/2014 | Prakash et al. |
| 2014/0296499 | A1 | 10/2014 | Chen et al. |
| 2014/0357588 | A1 | 12/2014 | Markosyan |
| 2015/0315623 | A1 | 11/2015 | Mao et al. |
| 2016/0186225 | A1 | 6/2016 | Mikkelsen |
| 2016/0298159 | A1 | 10/2016 | Tao et al. |
| 2017/0211113 | A1 | 7/2017 | Tao et al. |
| 2018/0320211 | A1 | 11/2018 | Du et al. |

FOREIGN PATENT DOCUMENTS

| CA | 2 913 252 A1 | 12/2014 |
| CN | 103031283 A | 4/2013 |
| CN | 103088041 A | 5/2013 |
| CN | 103179850 A | 6/2013 |
| CN | 103397064 A | 11/2013 |
| CN | 106471128 A | 1/2014 |
| CN | 103757074 A | 4/2014 |
| CN | 105200098 A | 12/2015 |
| JP | 2010-538621 | 12/2010 |
| JP | 2012-504552 A | 2/2012 |
| RU | 2 596 190 C9 | 10/2016 |
| WO | WO 2010/038911 A1 | 4/2010 |
| WO | WO 2011/046423 A1 | 4/2011 |
| WO | WO 2011/153378 A1 | 12/2011 |
| WO | WO 2012/103074 A2 | 8/2012 |
| WO | WO 2013/022989 A2 | 2/2013 |
| WO | WO 2013/096420 A1 | 6/2013 |
| WO | WO 2013/110673 A1 | 8/2013 |
| WO | WO 2013/176738 A1 | 11/2013 |
| WO | WO 2014/086890 A1 | 6/2014 |
| WO | WO 2014/122227 A2 | 8/2014 |
| WO | WO 2015/021690 A1 | 2/2015 |
| WO | WO 2015/094117 A1 | 6/2015 |
| WO | WO 2015/113231 A1 | 8/2015 |
| WO | WO2016/028899 A1 | 2/2016 |
| WO | WO 2016/054534 A1 | 4/2016 |
| WO | WO 2016/196345 A1 | 12/2016 |
| WO | WO 2017/031424 A1 | 2/2017 |

OTHER PUBLICATIONS

Genbank, "UDP-glycosyltransferase 76G1 [Stevia rebaudiana]," Accession No. AAR06912.1, accessed at http://www.ncbi.nlm.nih.gov/protein/AAR06912, accessed on May 26, 2016, 2 pages.
Genbank, "Os03g0702000 [Oryza saliva Japonica Group]," Accession No. NP_001051007.2, accessed at http://www.ncbi.nlm.nih.gov/protein/NP_001051007.2?report=genpept, accessed on May 26, 2016, 4 pages.
Masada, S., et al., "An efficient chemoenzymatic production of small molecule glucosides with in situ UDP-glucose recycling," *FEBS Letters* 581(13):2562-2566, Elsevier B.V., Netherlands (2007).
Ohta, M., et al., "Characterization of Novel Steviol Glycosides from Leaves of Stevia rebaudiana Morita," *J. Appl. Glycosci.* 57(3):199-209, The Japanese Society of Applied Glycoscience, Japan (2010).
Wang, Q.J., et al., "*Saccharomyces cerevisiae* surface expression of sucrose synthase," China resources biotechnology and enzyme engineering symposium proceedings (2005).
Wölwer-Rieck, U., "The leaves of Stevia rebaudiana (Bertoni), their constituents and the analyses thereof: a review," *J Agric Food Chem.* 60(4):886-895, American Chemical Society, United States (2012).
Co-pending Application, U.S. Appl. No. 16/343,335, inventors Tao, A., et al., filed Oct. 21, 2016 (Not Published).
Pearson, W.R., "An Introduction to Sequence Similarity ("Homology") Searching," *Curr Protoc Bioinformatic*, Author Manuscript, Jun. 3, Wiley, USA (2013).

(Continued)

*Primary Examiner* — Suzanne M Noakes
(74) *Attorney, Agent, or Firm* — Sterne, Kessler, Goldstein & Fox P.L.L.C.

(57) ABSTRACT

Provided is a method for preparing Rebaudioside J using an enzymatic method, comprising using rebaudioside A as a substrate, and making the substrate, in the presence of a glycosyl donor, react under the catalysis of a UDP-glycosyltransferase-con-taining recombinant cell and/or UDP-glycosyltransferase prepared therefrom to generate Rebaudioside J.

12 Claims, No Drawings

Specification includes a Sequence Listing.

(56) References Cited

OTHER PUBLICATIONS

Whisstock et al. Quarterly Reviews of Biophysics, "Prediction of protein function from protein sequence and suucture," 36(3): 307-340 (2003).
Witkowski et al., "Conversion of a beta-ketoacyl synthase to a malonyl decarboxylase by replacement of the active-site cysteine with glutamine," Biochemistry 38(36): 11643-11650 (1999).
Chen, R.R., "Permeability issues in whole-cell bioprocesses and cellular membrane engineering," Appl Microbial Biotechnol 74:730-738 (2007).
UniProtKB—F2DT21 (F2DT21_HORVD), May 31, 2011, accessed at http://www.uniprot.org/uniprot/F2DT21, 4 pages.
Co-pending Application, U.S. Appl. No. 15/932,218, inventors Anderson, A., et al., filed Aug. 19, 2016 (Not Published).
Co-pending Application, U.S. Appl. No. 16/380,678, inventors Tao, J., et al., filed Apr. 10, 2019 (Not Published).
Son, M.H. et al., "Production of Flavonoid O-Glucoside Using Sucrose Synthase and Flavonoid O-Glucosyltransferase Fusion Protein," J. Microbiol. Biotechnol. 19(7):709-12, Springer Nature, Switzerland (2009).
Mohamed, A.A. et al., "UDP-dependent glycosyltransferases involved in the biosynthesis of steviol glycosides," J Plant Physiol. 168(10):1136-41, Elsevier, Netherlands (2011).
Branden, C. et al., "Prediction, Engineering, and Design of Protein Structures," Introduction to Protein Structure, Garland Publishing Inc., New York, p. 247, 1991.
Studer, R.A. et al., "Residue mutations and their impact on protein structure and function:detecting beneficial and pathogenic changes," Biochem. J. 449:581-594, Biochemical Society, England (2013).
Co-pending Application, U.S. Appl. No. 16/343,339, inventors Tao, A., et al., filed Oct. 21, 2016 (Not Published).
Xu, L. et al., "Progress and strategies on bioethanol production from liganocellulose by consolidated bioprocessing (CBP) using *Saccharyomyces cerevisiae*," *Chinese Journal of Biotechnology* 26(7): 870-9 (2010).
English Translation of the Written Opinion for International Application No. PCT/CN2016/102948, State Intellectual Property Office of the P.R. China, China, dated Jul. 18, 2017, 3 pages.
English Translation of the International Preliminary Report on Patentability for International Application No. PCT/CN2016/102948, State Intellectual Property Office of the P.R. China, China, dated Apr. 23, 2019, 4 pages.
English Translation of the Written Opinion for International Application No. PCT/CN2016/102910, State Intellectual Property Office of the P.R. China, China, dated Jul. 14, 2017, 3 pages.
English Translation of the International Preliminary Report on Patentability for International Application No. PCT/CN2016/102910, State Intellectual Property Office of the P.R. China, China, dated Apr. 23, 2019, 4 pages.
English Translation of the Written Opinion for International Application No. PCT/CN2016/102942, State Intellectual Property Office of the P.R. China, China, dated Jul. 12, 2017, 4 pages.
English Translation of the International Preliminary Report on Patentability for International Application No. PCT/CN2016/102942, State Intellectual Property Office of the P.R. China, China, dated Apr. 23, 2019, 5 pages.
Supplementary European Search Report for EP Application No. EP 16 91 9469, Berlin, Germany, dated Jun. 24, 2020, 2 pages.
Supplementary European Search Report for EP Application No. EP 16 91 9379, Berlin, Germany, dated Jun. 18, 2020, 3 pages.

SEQUENCE LISTING

```
<160> NUMBER OF SEQ ID NOS: 2

<210> SEQ ID NO 1
<211> LENGTH: 1389
<212> TYPE: DNA
<213> ORGANISM: Artificial Sequence
<220> FEATURE:
<223> OTHER INFORMATION: Synthesized nucleotide sequence

<400> SEQUENCE: 1
atggacagcg gttactcttc tagctatgct gcggcagccg gtatgcacgt agttatttgt      60
ccgtggctcg ctttcggtca cctcctgccg tgcctggacc tggcgcagcg cctggcatct     120
cgtggtcacc gtgtcagttt cgttagcacg ccgcgtaaca tctcacgtct gccgccggtc     180
cgtccggctc tggccccgct ggttgcgttc gttgcgctac ctctgccgcg cgttgaaggc     240
ttaccggatg gcgcagagtc taccaacgac gtgccgcacg atcgcccgga tatggttgaa     300
ctccaccgcc gtgcatttga cggtctggca gctccgttct ccgaatttct gggtaccgcg     360
tgtgccgact gggtcatcgt agacgtattc caccactggg cagctgcagc ggctttagaa     420
cacaaagtac cgtgcgcaat gatgctgctg ggctctgctc acatgatcgc gtctattgcc     480
gaccgtcgtc tggaacgtgc agagaccgaa tctccagcgg cagccggtca gggccgtcct     540
gcagctgctc cgaccttcga agttgctcgt atgaagctca tccgcactaa aggttcttcc     600
ggtatgtcac tggcagagcg tttctcgctg acgctctccc gtagcagcct ggttgtgggg     660
cgctcctgcg tggaattcga accggaaact gtgccgctac tgtctaccct gcgtggcaag     720
ccgatcactt ttctgggtct catgccgcca ctgcacgaag gtcgccgcga agacggtgaa     780
gatgctacgg ttcgttggtt ggacgcccag ccggctaaaa gcgtcgtgta cgtagctctg     840
ggcagtgaag ttccattggg tgtcgagaaa gtgcatgaac tggctttggg tctggagctg     900
gctggcaccc gtttcctctg ggcactgcgt aagccgactg gtgtgtctga tgctgacctt     960
```

```
ctgccggctg gtttcgaaga acgtacccgt ggtcgcggcg tagtggcaac ccgctgggta    1020
ccgcagatgt ccatcctggc acacgctgct gttggcgcgt tcttaccca ctgcgggtgg     1080 aactctacaa tcgaaggcct gatgttcggc catcctctga ttatgctgcc aatcttcggt    1140
gatcagggtc cgaacgctcg tctgatcgaa gccaaaaacg ccggcttaca agtcgcacgc    1200
aacgacggcg atggttcttt cgatcgtgaa ggtgttgcgg cagctatccg tgcagtggct    1260
gtagaagaag agtcgagcaa agtgttccag gcaaaagcca aaagctgca ggaaatcgtt     1320 gcggacatgg cgtgccacga acgttacatc gatggcttta tccagcagct gcgctcctac    1380
aaagattaa                                                            1389
```

<210> SEQ ID NO 2
<211> LENGTH: 462
<212> TYPE: PRT
<213> ORGANISM: Artificial Sequence
<220> FEATURE:
<223> OTHER INFORMATION: Synthesized protein sequence

<400> SEQUENCE: 2

```
Met Asp Ser Gly Tyr Ser Ser Tyr Ala Ala Ala Gly Met His
1               5                   10                  15

Val Val Ile Cys Pro Trp Leu Ala Phe Gly His Leu Leu Pro Cys Leu
                20                  25                  30

Asp Leu Ala Gln Arg Leu Ala Ser Arg Gly His Arg Val Ser Phe Val
            35                  40                      45

Ser Thr Pro Arg Asn Ile Ser Arg Leu Pro Pro Val Arg Pro Ala Leu
        50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95

Asp Met Val Glu Leu His Arg Arg Ala Phe Asp Gly Leu Ala Ala Pro
            100                 105                 110

Phe Ser Glu Phe Leu Gly Thr Ala Cys Ala Asp Trp Val Ile Val Asp
        115                 120                 125

Val Phe His His Trp Ala Ala Ala Ala Leu Glu His Lys Val Pro
130                 135                 140

Cys Ala Met Met Leu Leu Gly Ser Ala His Met Ile Ala Ser Ile Ala
145                 150                 155                 160

Asp Arg Arg Leu Glu Arg Ala Glu Thr Glu Ser Pro Ala Ala Ala Gly
                165                 170                 175

Gln Gly Arg Pro Ala Ala Ala Pro Thr Phe Glu Val Ala Arg Met Lys
            180                 185                 190

Leu Ile Arg Thr Lys Gly Ser Ser Gly Met Ser Leu Ala Glu Arg Phe
        195                 200                 205

Ser Leu Thr Leu Ser Arg Ser Ser Leu Val Val Gly Arg Ser Cys Val
    210                 215                 220

Glu Phe Glu Pro Glu Thr Val Pro Leu Leu Ser Thr Leu Arg Gly Lys
225                 230                 235                 240

Pro Ile Thr Phe Leu Gly Leu Met Pro Pro Leu His Glu Gly Arg Arg
                245                 250                 255

Glu Asp Gly Glu Asp Ala Thr Val Arg Trp Leu Asp Ala Gln Pro Ala
            260                 265                 270

Lys Ser Val Val Tyr Val Ala Leu Gly Ser Glu Val Pro Leu Gly Val
        275                 280                 285
```

-continued

```
Glu Lys Val His Glu Leu Ala Leu Gly Leu Glu Leu Ala Gly Thr Arg
    290             295             300
Phe Leu Trp Ala Leu Arg Lys Pro Thr Gly Val Ser Asp Ala Asp Leu
305             310             315                         320
Leu Pro Ala Gly Phe Glu Glu Arg Thr Arg Gly Arg Gly Val Val Ala
                325             330             335
Thr Arg Trp Val Pro Gln Met Ser Ile Leu Ala His Ala Ala Val Gly
            340             345             350
Ala Phe Leu Thr His Cys Gly Trp Asn Ser Thr Ile Glu Gly Leu Met
            355             360             365
Phe Gly His Pro Leu Ile Met Leu Pro Ile Phe Gly Asp Gln Gly Pro
    370             375             380
Asn Ala Arg Leu Ile Glu Ala Lys Asn Ala Gly Leu Gln Val Ala Arg
385             390             395                         400
Asn Asp Gly Asp Gly Ser Phe Asp Arg Glu Gly Val Ala Ala Ala Ile
            405             410             415
Arg Ala Val Ala Val Glu Glu Glu Ser Ser Lys Val Phe Gln Ala Lys
            420             425             430
Ala Lys Lys Leu Gln Glu Ile Val Ala Asp Met Ala Cys His Glu Arg
        435             440             445
Tyr Ile Asp Gly Phe Ile Gln Gln Leu Arg Ser Tyr Lys Asp
    450             455             460
```

ENZYMATIC METHOD FOR PREPARING REBAUDIOSIDE J

REFERENCE TO SEQUENCE LISTING SUBMITTED ELECTRONICALLY

The content of the electronically submitted sequence listing, (file name: 3711_9320000_SequenceListing.txt; size: 6,304 bytes; and date of creation: Apr. 15, 2019), filed herewith, is incorporated herein by reference in its entirety.

TECHNICAL FIELD

The present invention relates to a method for preparing Rebaudioside J, and in particular, relates to a biological method for preparing Rebaudioside J.

BACKGROUND

Sweetening agents are a class of food additives that have wide applications in the production of food, beverages, and candies. They may be added in the food production process, or alternatively may be used through appropriate dilution as a substitute for sucrose in household baking. Sweetening agents include natural sweetening agents, for example, sucrose, high fructose corn syrup, honey, etc., and artificial sweetening agents, for example, aspartame, saccharine, etc. Steviosides are a class of natural sweetening agents extracted from the plant *Stevia rebaudiana*, and are widely used in food products and beverages at present. The extract of *Stevia rebaudiana* contains a variety of steviosides comprising rebaudioside. Naturally extracted steviosides have great differences in ingredients across different batches, and need subsequent purification.

The content of Rebaudioside J found in the steviosides of the *Stevia* leaves does not exceed 0.5%; thus, it is extremely difficult to obtain a extract of Rebaudioside J with high purity using the conventional method. Therefore, there are limited the in-depth studies of Rebaudioside J, and the commercial application of Rebaudioside J is hindered.

SUMMARY

The technical problem to be solved by the present invention is to overcome the defects in the prior art. The present invention achieves so by providing a method for preparing Rebaudioside J using an enzymatic method. With such a method, rebaudioside J product with high purity can be produced at a lower cost and with a shorter production cycle.

The following technical solution is employed by the present invention to solve the technical problem described above.

Provided is a method for preparing Rebaudioside J using an enzymatic method, wherein in the method, rebaudioside A is used as a substrate; and in the presence of a glycosyl donor, Rebaudioside J is produced by means of reaction under the catalysis of recombinant cells containing UDP-glycosyltransferase and/or UDP-glycosyltransferase prepared therefrom. UDP-glycosyltransferase (i.e., uridine diphosphoglycosyltransferase), also referred to as UGT, is already well-known.

Preferably, the glycosyl donor is a rhamnosyl donor.

More preferably, the rhamnosyl donor is a UDP-rhamnose.

Preferably, the UDP-glycosyltransferase is a UGT-B from *Oryza sativa* (rice).

Preferably, the amino acid sequence of UGT-B from *Oryza sativa* is at least 60% consistent with Sequence 2 as shown in the Sequence Listing.

More preferably, the amino acid sequence of UGT-B from *Oryza sativa* is at least 70% consistent with Sequence 2 as shown in the Sequence Listing.

Further, the amino acid sequence of UGT-B from *Oryza sativa* is at least 80% consistent with Sequence 2 as shown in the Sequence Listing.

Furthermore, the amino acid sequence of UGT-B from *Oryza sativa* is at least 90% consistent with Sequence 2 as shown in the Sequence Listing.

According to one example, the amino acid sequence of UGT-B from *Oryza sativa* is completely identical with Sequence 2 as shown in the Sequence Listing.

According to the present invention, the reaction is carried out in an aqueous system at a temperature of 4-50° C. and a pH of 5.0 to 9.0. Preferably, the reaction is carried out in an aqueous system at a temperature of 35-45° C. and a pH of 7.5 to 8.5. More Preferably, the reaction is carried out at a temperature of below 40° C. and a pH of below 8.0.

More Preferably, the reaction is carried out in a phosphate buffer solution.

More Preferably, the reaction system contains recombinant cells of UDP-glycosyltransferase and a cell-permeating agent, and the reaction is carried out in the presence of the cell-permeating agent. Further, the cell-permeating agent is toluene, and the volume ratio concentration of toluene in the reaction system is 1-3%. Furthermore, the volume ratio concentration of toluene is 2%.

More Preferably, all the raw materials used in the reaction are added into a reaction kettle to be uniformly mixed and then placed at a set temperature for reaction while stirring. After the reaction is completed, a Rebaudioside J product which can meet the requirements for use can be obtained through purification-processing. A specific purification method is through post-processing including resin isolation; and a Rebaudioside J product with a purity as high as 95% can be obtained.

Preferably, the recombinant cell is a microbial cell.

More Preferably, the microorganism is *Escherichia coli, Saccharomyces cerevisiae*, or *Pichia pastoris*.

By means of the foregoing technical solution, the present invention has the following advantages in comparison with the prior art:

The method of preparing Rebaudioside J using the enzymatic method provided by the present invention has important application values. As the substrate Rebaudioside A can be obtained in large quantities through using the enzymatic method, the production of Rebaudioside J is no longer limited by the quantity of raw materials. The production cost is thus greatly reduced. It should also be considered that because of the low content of Stevioside in the plant, and there are many Steviosides with different structures, it is rather difficult to extract a product with high purity. When compared with the prior art for extracting Rebaudioside J from *Stevia* leaves, the present invention provides a product with a higher purity by adopting the enzymatic synthesis method, which will promote the research and application of novel Stevioside Rebaudioside J.

DETAILED DESCRIPTION OF THE INVENTION

For the structural formulas of Rebaudioside A and Rebaudioside J, see Formulas I and II respectively.

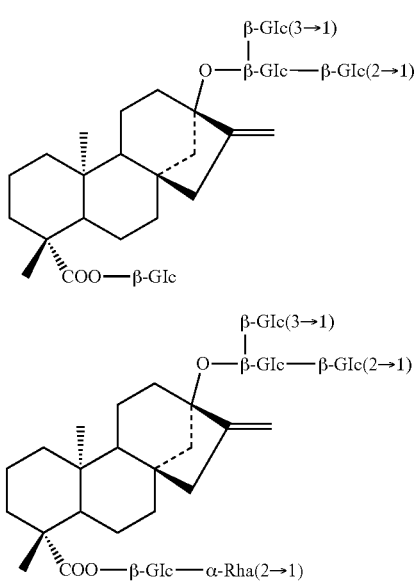

The main synthesis route of Rubadioside J as provided by the present invention is as follows:

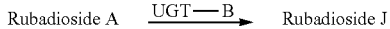

The UGT-B adopted in the present invention may exist in the form of lyophilized enzyme powder or in the recombinant cells.

The method for obtaining the UGT-B is as follows:
a recombinant *Escherichia coli* (or the other microorganisms) expression strain of UGT-B is obtained by utilizing molecular cloning technique and genetic engineering technique; then the recombinant *Escherichia coli* is fermented to obtain recombinant cells containing UGT-B, or to prepare and obtain lyophilized powder of UGT-B from the above noted recombinant cells.

Both the molecular cloning technique and the genetic engineering technique described in the present invention are already well-known. The molecular cloning technique may be found in *Molecular Cloning: A Laboratory Manual* (3rd Edition) (J. Sambrook, 2005).

The expression steps of the recombinant strain herein constructed by employing genetic engineering technique are as follows:

(1) (according to Sequence 1 and Sequence 2 as shown in the Sequence Listing) the required gene fragment is genetically synthesized, ligated into a pUC57 vector, while respectively adding NdeI and BamHI enzyme cutting sites at the two ends;

(2) each gene fragment is inserted into the corresponding enzyme cutting site of the expression vector pET30a through double digestion and ligation, so that each gene is placed under the control of T7 promoter;

(3) the recombinant plasmid is transformed into *Escherichia coli* BL21 (DE3); the expression of the target protein is induced by utilizing IPTG; and then the expression strains of the recombinant *Escherichia coli* of UGT-B is obtained.

The steps for preparing the recombinant cells containing UGT-B and the lyophilized powder of UGT-B by utilizing the expression strains of the recombinant *Escherichia coli* containing UGT-B are as follows:

the recombinant *Escherichia coli* expression strains containing UGT-B were inoculated into 4 ml of liquid LB medium according to a proportion of 1%; shake cultivation was carried out at 37° C. (at 200 rpm) overnight; the substance cultivated overnight was taken and inoculated into 50 ml of liquid medium according to a proportion of 1%; shake cultivation was carried out at 37° C. (at 200 rpm) overnight until the OD600 value reached 0.6-0.8; then IPTG with a final concentration of 0.4 mM was added in at 20° C. for shake cultivation overnight. After the induction is completed, the cells were collected through centrifugation (8,000 rpm, 10 min); then the cells were resuspended with 5 ml 2 mmol/L of phosphate buffer liquid (pH7.0), to obtain the recombinant cells; then the cells were ultrasonically disrupted in ice bath; the homogenate was centrifuged (8,000 rpm, 10 min); and the supernatant was collected and lyophilized for 24 h to obtain the lyophilized powder. The present invention is further described in details in combination with specific examples.

Example 1: Preparation of the Recombinant *Escherichia Coli* Cells Containing UGT-B According to Sequence 3 and Sequence 4, the UGT-B gene fragment was genetically synthesized, while respectively adding NdeI and BamHI enzyme cutting sites at the two ends, and ligated to the pUC57 vector (produced by Suzhou Jin Wei Zhi Biotech. Co., Ltd.). The UGT gene segment was enzyme cut with restriction endonucleases NdeI and BamHI; and then the segments were recovered and purified; a T4 ligase was added to ligate the segments into the corresponding enzyme cutting sites of pET30a, in order to transform the BL21 (DE3) strains.

The UGT strains were inoculated into 4 ml of liquid LB medium according to a proportion of 1%; shake cultivation was carried out at 37° C. (at 200 rpm) overnight; the substance cultivated overnight was taken and inoculated into 50 ml of liquid LB medium according to a proportion of 1%; shake cultivation was carried out at 37° C. (at 200 rpm) overnight until the OD600 value reached 0.6-0.8; then IPTG with a final concentration of 0.4 mM was added in at 20° C. for shake cultivation overnight. After the induction is completed, the cells were collected through centrifugation (8,000 rpm, 10 min); and the collected cells were resuspended with 5 ml 2 mol/L of phosphate buffer (pH 7.0) to obtain the recombinant cells containing UGT-B for catalysis.

Example 2 Preparation of the Lyophilized Powder of UGT-B

The recombinant cells containing UGT-B prepared in example 3 were ultrasonically disrupted in ice bath; the homogenate was centrifuged (8,000 rpm, 10 min); and the supernatant was collected and lyophilized for 24 h to obtain the lyophilized powder of UGT-B.

Example 3: Synthesis of Rebaudioside J Under the Catalysis of UDP-Glycosyltransferase with Rebaudioside A as the Substrate In this example, lyophilized powder of UGT-B prepared according to the method of Example 2 was used for the catalysis and synthesis of Rebaudioside J.

1 L 0.05 mol/L of phosphate buffer solution (pH8.0), 2 g of UDP Rhamnose, 1 g of Rebaudioside A, 10 g of lyophilized powder of UGT-B were sequentially added into the reaction system, and placed into a water bath at 40° C. after evenly mixing, for reaction for 24 h while stirring at 300 rpm. After the reaction is completed, 500 µl of the reactant solution was added into anhydrous methanol of the equal volume for uniformly mixing; then it was centrifuged at 8,000 rpm for 10 min; and a high performance liquid chromatography was used to detect the supernatant filtration membrane (chromatographic conditions: column: Agilent eclipse sb-C18 4.6×150 mm; detection wavelength: 210 nm; mobile phase: acetonitrile: deionized water=24%: 76%; flow rate: 1.0 mL/min; column temperature: 30° C.). The conversion rate of Rebaudioside A was greater than 90%. After the supernatant was purified by post-processing such as isolating by silica resin and crystallizing, 0.52 g of Rebaudioside J was obtained, and the purity of which was greater than 95%.

Example 4: Synthesis of Rebaudioside J Under the Catalysis of Recombinant Cells of UDP-Glycosyltransferase with Rebaudioside A as the Substrate In this example, recombinant cells containing UGT-B prepared according to the method of Example 1 was used for the catalysis and synthesis of Rebaudioside J.

1 L 0.05 mol/L of phosphate buffer solution (pH8.0), 2 g of UDP Rhamnose, 1 g of Rebaudioside A, 20 ml of toluene, 40% of UGT-B whole cells were sequentially added into the reaction system, and placed into a water bath at 40° C. after uniformly mixing, to react for 24 h while stirring at 300 rpm. After the reaction is completed, 500 µl of the reactant solution was taken, and the supernatant was added with anhydrous methanol of the equal volume for uniformly mixing; then it was centrifuged at 8,000 rpm for 10 min; and a high performance liquid chromatography was used to detect the supernatant filtration membrane (chromatographic conditions: column: Agilent eclipse sb-C18 4.6×150 mm; detection wavelength: 210 nm; mobile phase: acetonitrile: deionized water=24%: 76%; flow rate: 1.0 mL/min; column temperature: 30° C.). The conversion rate of Rebaudioside A was greater than 90%. After the supernatant was purified by post-processing such as isolating by silica resin and crystallizing, 0.49 g of Rebaudioside J was obtained, and the purity of which was greater than 95%.

The above-described examples are merely for the illustration of the technical concept and features of the present invention. The object of providing examples is only to allow those skilled in the art to understand the present invention and implement it accordingly; the scope of the present invention is not limited thereto. Any equivalent variations or modifications derived from the essence of the present invention shall fall within the protection scope of the present invention.

The invention claimed is:

1. An enzymatic method for preparing Rebaudioside J, the method comprising reacting rebaudioside A with a rhamnosyl donor in a reaction system comprising:

Recombinant cells comprising a UDP-glycosyltransferase and/or a UDP-glycosyltransferase prepared therefrom, wherein the UDP-glycosyltransferase has at least 80% sequence identity to the amino acid sequence of SEQ ID NO: 2.

2. The method of claim 1, wherein the rhamnosyl donor is a UDP-rhamnose.

3. The method of claim 1, wherein the UDP-glycosyltransferase is UGT-B from *Oryza sativa*.

4. The method of claim 1, wherein the reaction system is aqueous and has a temperature of 35-45° C. and a pH of 7.5 to 8.5.

5. The method of claim 4, wherein the reaction system comprises a phosphate buffer solution.

6. The method of claim 4, wherein the reaction system further comprises a cell-permeabilizing agent.

7. The method of claim 6, wherein the cell-permeabilizing agent is toluene and wherein the toluene has a concentration by volume of 1-3%.

8. The method of claim 1, wherein the recombinant cell is a cell of a microorganism.

9. The method of claim 8, wherein the microorganism is *Escherichia coli, Saccharomyces cerevisiae*, or *Pichia pastoris*.

10. The method of claim 1, further comprising purifying the rebaudioside J via resin isolation.

11. The method of claim 10, wherein the rebaudioside J purified via resin isolation has a purity greater than 95%.

12. The enzymatic method of claim 1, wherein the UDP-glycosyltransferase comprises SEQ ID NO: 2.

* * * * *